United States Patent [19]

Slininger et al.

[11] Patent Number: 4,962,027

[45] Date of Patent: Oct. 9, 1990

[54] PRODUCTION OF 3-HYDROXYPROPIONALDEHYDE FROM GLYCEROL BY *KLEBSIELLA PNEUMONIAE*

[75] Inventors: Patricia J. Slininger, Metamora; James E. Vancauwenberge, Normal; Rodney J. Bothast, East Peoria, all of Ill.

[73] Assignee: The United States of America as represented by the Secretary of Agriculture, Washington, D.C.

[21] Appl. No.: 894,140

[22] Filed: Aug. 7, 1986

[51] Int. Cl.$^5$ .......................... C12P 7/24; C12P 7/02; C12N 1/38; C12N 1/12
[52] U.S. Cl. .................................. 435/147; 435/155; 435/244; 435/252.1
[58] Field of Search ............... 435/147, 155, 244, 852, 435/252.1, 828

[56] References Cited

PUBLICATIONS

Slininger et al., *Appl. and Environ. Microbiol.*, Jul. 1983, pp. 62–67, vol. 46.
R. H. Abeles, A. M. Brownstein, and C. H. Randles, "B-Hydroxypropionaldehyde, an Intermediate in the Formation of 1,3-Propanediol by *Aerobacter aerogenes*," *Biochim. Biophys. Acta.*, 41:530–531 (1960).
P. J. Slininger, R. J. Bothast, and K. L. Smiley, "Production of 3-Hydroxypropionaldehyde from Glycerol," *Applied and Environmental Microbiology*, 46(1):62–67 (1983).
P. J. Slininger and R. J. Bothast, "Optimizing Aerobic Conversion of Glycerol to 3-Hydroxypropionaldehyde," *Applied and Environmental Microbiology*, 50(6), 1444–1450 (1985).

*Primary Examiner*—Elizabeth C. Weimar
*Assistant Examiner*—Irene Marx
*Attorney, Agent, or Firm*—M. Howard Silverstein; Curtis P. Ribando; Margaret A. Connor

[57] ABSTRACT

A method is disclosed for producing 3-hydroxypropionaldehyde (3-HPA) from glycerol by culturing the bacterium *Klebsiella pneumoniae* having the identifying characteristics of NRRL B-4011, under aerobic conditions, in an aqueous nutrient medium containing glycerol and a compound that causes 3-HPA to be accumulated by blocking the conversion of 3-HPA to trimethylene glycol. This process is particularly useful for the production, from renewable resources, of acrylic acid, an industrially important plymerizable monomer used in the manufacture of synthetic polymers and plastics and which is presently derived from fossil fuel sources.

3 Claims, 1 Drawing Sheet

PRODUCTION OF 3-HYDROXYPROPIONALDEHYDE FROM GLYCEROL BY *KLEBSIELLA PNEUMONIAE*

BACKGROUND OF THE INVENTION

1. Field of the Invention

This invention relates to the microbial production of 3-hydroxypropionaldehyde from glycerol under aerobic conditions using a strain of *Klebsiella pneumoniae*.

2. Description of the Art

Approximately 10 percent of all petroleum and natural gas consumed in the United States is used in the production of organic chemicals. Acrylic acid, an industrially important polymerizable monomer useful in the manufacture of synthetic polymers and plastics is currently derived from petroleum. To reduce dependence on fossil oil reserves, new energy-efficient routes are needed that utilize renewable resources as feedstocks for the synthesis of acrylic acid and other petroleum-derived chemicals. Glycerol which is easily accessible from ubiquitous plant and animal lipids, is such a feedstock. While it is known that acrylic acid can be prepared by chemical oxidation of 3-hydroxypropionaldehyde (3-HPA), presently, no commercial source of 3-HPA exists. One suggested potential source for 3-HPA is through fermentation of glycerol. Abeles et al. (*Biochim. Biophys. Acta.* 41: 530–531 (1960)) positively identified 3-HPA as a metabolic intermediate in the conversion of glycerol to trimethylene glycol by *Klebsiella oxytoca* NRRL B-199 (previously classified *K. pneumoniae* and *Aerobacter aerogenes*) grown anaerobically on glycerol. Normally, 3-HPA is not an end product of bacterial glycerol dissimilation, but an intermediate which must be trapped and so forced to accumulate by manipulation of the metabolism. Abeles et al., supra, noted that 3-HPA accumulated when anaerobic fermentation of glycerol was carried out in the presence of semicarbazide. Fermentation studies carried out by Slininger et al. (*Applied and Environmental Microbiology* 46(1): 62–67 (1983)) using *K. oxytoca* NRRL B-199 under aerobic conditions determined that 55% of the theoretical maximum concentration of 3-HPA could be realized by fermentation of glycerol (30 g/liter) when semicarbazide hydrochloride concentration was optimized at 26.8 g/liter. Further studies by Slininger et al. (*Applied and Environmental Microbiology*, 50(6): 1444–1450 (1985)) indicated that cell growth and glycerol dehydratase induction required at least 48 to 72 hours, and peak 3-HPA accumulation reached 15–20 g/liter at a specific production rate of 0.1 to 0.3 gram/gram biomass/hour.

Pathways responsible for glycerol dissimilation by *K. oxytoca* have been described. After transport into the cell, glycerol dissimilation is believed to occur via either of two inducible pathways summarized in FIG. 1, the glycerophosphate (glp) or the dihydroxyacetone (dha) system. 3-HPA is an intermediate of the dha path which coproduces trimethylene glycol (TMG) and dihydroxyacetone phosphate via NAD-coupled reactions. Regulatory mechanisms governing the course of dissimilation are complex. Carbon source and hydrogen acceptors such as oxygen are influential. Respiratory repression of enzyme induction may regulate use of the glp versus dha pathway in *K. oxytoca* strains. Oxygen-mediated deactivation of sYnthesized dehydratases and dehydrogenases may also influence observed enzyme activities.

Deviations from common regulatory mechanisms documented for *K. oxytoca* strains, such as NRRC B-199 (ATCC 8724), have been reported (Slininger et al, 1985, supra). Attempts to convert glycerol to 3-HPA by glycerol dehydratase isolated from *Lactobacillus* sp. strain NRRL B-1720 were unsatisfactory because enzyme activity was lost within 60 to 90 minutes after the reaction initiation (Slininger et al., 1983, supra).

SUMMARY OF THE INVENTION

We have discovered a strain of *Klebsiella pneumoniae* which has the ability to produce 3-hydroxypropionaldehyde (3-HPA) from glyorol under aerobic conditions rapidly and in good quantity. In the method of the invention, the bacterium *Klebsiella pneumoniae* having the identifying characteristics of strain NRRL B-4011 is cultured in the presence of glycerol and a compound that causes 3-HPA to be accumulated.

Surprisingly, strain NRRL B-4011 is significantly superior to *K. oxytoca* NRRL B-199, the only strain previously identified as producigg 3-HPA. Using *K. pneumoniae* NRRL B-4011, cell growth and dehydratase induction in the induction step are complete within half the time required for *K. oxytoca* NRRL B-199. In the 3-HPA accumulation step, up to twice the 3-HPA concentration is produced by strain NRRL B-4011 at almost three times the rate observed for strain NRRL B-199.

The unexpectedness of this discovery is further shown by the fact that of the 55 bacterial strains tested by us for conversion of glycerol to 3-HPA under aerobic conditions, only five tested positive for 3-HPA production. Of the strains which tested positive, strain NRRL B-4011 was significantly superior with respect to both rate of conversion of glycerol to 3-HPA and yield of 3-HPA. The next best strain was NRRL B-199.

In accordance with this discovery, it is an oject of the invention to provide a means to produce 3-HPA in high yield and at a rapid rate from aerobic fermentation of glycerol with *K. pneumoniae* having the identifying characteristics of strain NRRL B-4011.

It is also an object of the invention to produce high yields of 3-HPA by a commercially feasible fermentation process.

Another important object of the invention is to provide a method for the microbial conversion of 3-HPA from biomass and thereby provide a commercial source of 3-HPA for the production of acrylic acid and other useful industrial chemicals.

Other objects and advantages of the invention will become readily apparent from the ensuing description.

DETAILED DESCRIPTION OF THE INVENTION

The Microorganism

Figure 1:
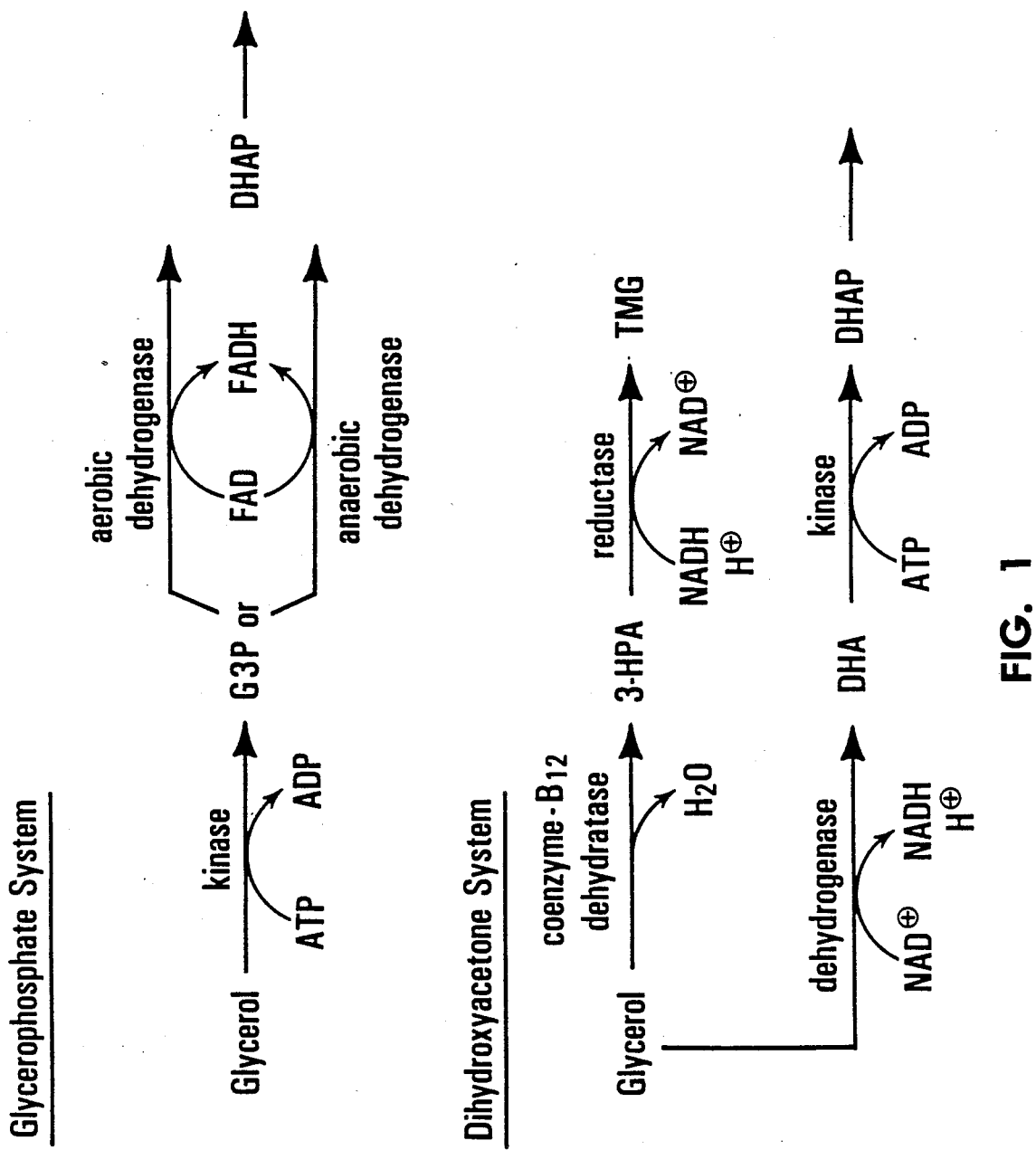
FIG. 1 shows the dual metabolic pathways involved in glycerol dissimilation by *K. oxytoca*.

The bacterium *Klebsiella pneumoniae* NRRL B-4011 (previously classified *Enterobacter aerogenes*) for use in the method of the invention was obtained from the U.S. Department of Agriculture, Agricultural Research Culture Collection, Northern Regional Research Center, Peoria, Ill. A culture is on permanent deposit with the NRRL culture collection and is available under the accession No. NRRL B-4011.

*K. pneumoniae* NRRL B-4011 is a nonmotile, capsulated rod. When grown on meat extract medium, it produces a dome-shaped, glistening, sticky colony. This bacterium originated from the collection of R. J. Williams, University of Texas, who first deposited it in the American Type Culture Collection as strain 9621. Since deposit in ATCC, it has been passed to the Faculty of Agriculture, Tokyo, and from there to the Institute for Fermentation, Osaka, (IFO), in 1954. The culture at NRRC was received from IFO.

Maintenance of stock cultures of NRRL B-4011: Stock cultures of the bacterium are maintained on slants composed of an appropriate growth medium, such as tryptone glucose yeast (TGY) medium, supplemented wih agar. After inoculation, slants are incubated at about 35° to 37° C. until sufficient cell growth covers the surface (about 24–48 hours). Mature slants can be stored at room temperature for 1 to 2 weeks or in a refrigerator for 2 to 4 weeks for future use in inoculating other slants and seed cultures.

Maintenance of seed cultures of NRRL B-4011: A slant culture is initially used to inoculate a seed culture which then serves as inoculum for subsequent seed cultures. In this way, seed culuures can be transferred one or more times before being used to inoculate a process culture. It is generally good practice to initiate a seed culture series once a week from slant, however. The seed culture medium is the same as that used in the production of cells for converting glycerol to 3-HPA as described below. Seed cultures are incubated aerobically at about 35° to 37° C. on a mechanical shaker for about 24 hours before being transferred or used to initiate production of 3-HPA.

Production of 3-HPA

3-HPA is produced by culturing the bacterium *K. pneumoniae* having the identifying characteristics of strain NRRL B-4011 under aerobic conditions in the presence of glycerol and a compound that causes 3-HPA to be accumulated.

In the preferred method of the invention, the process is carried out in two steps. In step 1, NRRL B-4011 is cultured to obtain efficient cell growth and induction of the dehydratase enzyme. In the second step, the cells from step 1 are incubated in an aqueous medium which contains glycerol as a carbon source and which contains a compound which "traps" 3-HPA, that is, causes 3-HPA to be accumulated by blocking the conversion of 3-HPA to trimethylene glycol (TMG).

The conditions for step 1 are as follows. NRRL B-4011 is grown aerobically in a suitable aqueous culture medium which contains sources of carbon, nitrogen, and inorganic salts assimilable by the microorganism. The medium must contain a carbon source which induces the production of the enzyme, dehydratase. Such carbon sources are glycerol, 1,2-propanediol and 1,2-ethanediol. The carbon source for induction of dehydratase should be present in the growth medium in an amount sufficient to induce dehydratase throughout the cell growth step. Glycerol is the preferred carbon source due to its ready availability and lower cost. In general, a concentration of about 10 g/liter to 100 g/liter of glycerol (or other carbon source named above) in the culture medium provides efficient cell production and dehydratase induction. The concentration of carbon source for induction of dehydratase depends on the presence of other carbon sources in the medium, such as glucose, which, until completely consumed, repress dehydratase formation as shown in Table 1 below. It is preferred that glucose or other carbon sources which repress dehydratase formation, are kept to a minimum to avoid delay of enzyme induction.

Many inorganic and proteinaceous materials may be used as nitrogen sources in the growth process. Suitable nitrogen sources include, for example, sources of nitrate or ammonium ions, urea, yeast extract, beef extract, proteose peptone, soybean meal, hydrolysates of casein, distiller's solubles, and the like, provided they are not heavily contaminated with glucose, which is a catabolite repressor of dehydratase induction.

Among the inorganic salts that can be incorporated into the nutrient medium are the customary salts capable of yielding calcium, zinc, iron, manganese, magnesium, copper, cobalt, phosphorous, sulfate, chloride, borate, and like ions.

Cell growth in step 1 can be effected at any temperature conducive to satisfactory growth of the bacterium, for example between about 20° to 40° C., and preferably at 28° to 30° C. The pH of the nutrient medium suitable for growing *K. pneumoniae* NRRL B-4011 can vary from about 5 to 10. A pH of 6–7 is preferred. Ordinarily, optimum cell growth and dehydratase induction is obtained in about 24 to 48 hours.

In the second step, the cells grown in step 1 are harvested and then further incubated under aerobic conditions in an aqueous medium which contains glycerol as a carbon source and which contains a compound that causes 3-HPA to be accumulated, for example, semicarbazide hydrochloride. Glycerol should be present in the growth medium in an amount sufficient for efficient conversion of 3-HPA by the cells without inhibiting the production of 3-HPA. Concentrations of up to 150 g/liter of glycerol provide satisfactory production of 3-HPA. The preferred concentration range of glycerol is 30 to 70 g/liter. Sufficient semicarbazide must be present in the medium to cause 3-HPA to be accumulated by preventing the metabolism of 3-HPA to TMG. Concentrations of about 10 to 50 g/liter semicarbazide hydrochloride are suitable for trapping 3-HPA. The preferred concentration range is 30 to 50 g/liter semicarbazide. Production of 3-HPA can be effected at temperatures of about 20° to 40° C., and preferably 28° to 30° C. The pH of the medium can vary from about 5 to 10. The preferred pH is 6–7. For rapid conversion of glycerol to 3-HPA, cell concentration should be at least about 1 g/liter cells, and preferably 3–15 g/liter cells.

Small scale production of 3-HPA can be accomplished as follows: aerobic growth of the cell crop on a suitable growth medium, as described above, followed by fermentation of glycerol to 3-HPA by the cell crop resuspended in a buffer solution supplemented with glycerol and a 3-HPA trapping agent. The first step is begun by inoculating a sterilized flask of growth medium with a seed culture. Flasks are incubated on a mechanical shaker in a constant temperature chamber at 20° to 40° C., but preferably at 28°–30° C., for 24 hours or until satisfactory cell growth and dehydratase induction have occurred. At the end of the first step, cells are harvested, such as by filtration or centrifugation, and then used to start the second step upon resuspension in a buffered solution of glycerol and an appropriate trapping agent, such as semicarbazide hydrochloride. During the second incubation step, 3-HPA accumulates in flask cultures aerated by shaking when the following conditions are used: 20–40° C., 10–50 g/liter semicarbazide, up to 150 g/liter glycerol, pH 5–10, and over 1 g/liter cells.

For large scale work, it is preferable to conduct the two-step process in suitable tanks provided with agitators and a means of aeration. A continuous separator of suitable size may be used to harvest the cells from the first tank for inoculation of the second tank. Growth medium and buffered semicarbazide-glycerol solution may be prepared and sterilized in their respective tanks by heating at temperatures up to 121° C. Upon cooling, the tanks are ready for inoculation. The same incubation conditions suitable for the small scale process may be used to achieve 3-HPA accumulation during the large scale process.

It should be noted that while a two-step process is preferred, production of 3-HPA using NRRL B-4011 may be carried out wherein the dehydratase induction step and conversion of glycerol to 3-HPA and trapping of 3-HPA step are carried out as a single step process.

Isolation of 3-HPA

At the completion of or point of optimum 3-HPA accumulation, 3-HPA may be converted to its semicarbazone derivative by heating the cell-free reaction mixture to 100° C. and then allowing it to cool gradually. Crystals of the semicarbazone will precipitate and may be removed by filtration or centrifugation. The semicarbazone can be purified by recrystallization from water or 25–50% ethanol. Other purification techniques commonly applied to semicarbazones may also be used. At this point the semicarbazone may be stored or used in the production of acrylic acid after acidifying an aqueous semicarbazone suspension to release the 3-HPA. The concentration of the aqueous semicarbazone may be adjusted to achieve the desired 3-HPA concentration upon acidification.

Production and Polymerization of Arcylic Acid

Free 3-HPA obtained by the above treatment, which provides for purification, storage, and concentration, may be dehydrated to acrolein in hot, low pH aqueous solutions. Acrolein may, in turn, be oxidized to acrylic acid by addition of an oxidant like Tollen's reagent (Ag$(NH_3)_2^+$). Polymerization of acrylic acid molecules may be initiated upon generation of free radicals by, for example, treatment with peroxide. Upon precipitation, the polymer may be harvested by centrifugation or filtration.

Comparison With NRRL B-199

Slininger et al., 1985, supra, which reports optimization of conversion of glycerol to 3-HPA by *K. oxytoca* NRRL B-199, indicated that optimum cell growth and glycerol dehydratase induction in the dehydratase induction step required at least 48 to 72 hours, and that, in the second step, peak 3-HPA accumulation reached 15–20 g/liter at a specific production rate of 0.1 to 0.3 g/g biomass/hour.

As shown by the data in Tables 1 and 2, *K. pneumoniae* NRRL B-4011 is significantly superior to NRRL B-199 for conversion of glycerol to 3-HPA. Specifically, using NRRL B-4011 first step cell growth and dehydratase induction are complete after only 24–48 hours, and in the second step, peak 3-HPA accumulation reaches 15 to 46 g/liter at a specific production rate of 0.3 to 0.8 g/g biomass/hour. As can be seen, NRRL B-4011 cells can be harvested about 24 hours earlier for use in the second step where up to twice the 3-HPA concentration is produced at almost three times the rate observed for NRRL B-199.

The following example is presented to further illustrate the invention and are not intended to limit the scope of the invention which is defined by the claims.

EXAMPLE

A. Culture Maintenance. Stock cultures of biologically pure samples of *K. pneumoniae* NRRL B-4011 were maintained at 32° C. on agar slants containing 5.0 g tryptone, 5.0 g yeast extract, 1.0 g $K_2HPO_4$, and 1.0 g glucose per liter at pH 7.

B. Cell Growth and Induction of Dehydratase. Bacteria from slants were propagated on a beef extract (MRS) growth medium having a pH of 6.2 to 6.8 and the following composition per liter:

| | |
|---|---|
| Protease Peptone #3 | 10.0 g |
| Beef Extract | 10.0 g |
| Yeast Extract | 5.0 g |
| Glycerol | 50.0 g[a] |
| Na Acetate | 5.0 g |
| Ammonium Citrate | 2.0 g |
| Tween 80 | 1.0 g |
| $MgSO_4.7H_2O$ | 0.1 g |
| $MnSO_4.H_2O$ | 0.1 g |
| $K_2HPO_4$ | 2.0 g |

[a]Precultures; 100 g/liter were used in step 1 in cell growth fermentors.

A 50 ml preculture (50 g glycerol/liter) grown in a 125-ml Erlenmeyer flask for 24 hours at 30° C. and agitated at 150 rpm was used to initiate each 10 liter batch culture (100 g glycerol/liter). These 10 liter cultures for cell propagation were then incubated at 30° C. and 150 rpm for 24 hours in 10 liter fermentors until harvest.

C. Cell Harvest and Fermentation in the Presence of Semicarbazide Hydrochloride. After 24 hours, a Sharples Centrifuge was used to concentrate the culture to a paste which was resuspended in a pH 8.9 sterile buffer solution containing 17.4 g $K_2HPO_4$ per liter of distilled water. As a standard procedure, glycerol (3.0 g) and 2.68 g of semicarbazide hydrochloride were combined with appropriate volumes of cell suspension, buffer solution, and 10 N KOH to form a 100 ml fermentation mixture with an optical density of 30 at 620 nm (equivalent to 9.3 g dry cell mass per liter) and pH 6.2. Fermentations were carried out aerobically at 30° C. in 250-ml flasks shaken at 150 rpm in a New Brunswick Psycrotherm. To moniter the time courses of the fermentation, samples were drawn and analyzed for 3-HPA, biomass, and glycerol content.

D. Experimental Variables. Using this standard procedure as the control, experiments were conducted in which various growth and fermentation conditions were each tested separately to determine their influence on fermentation performance. Variables in the cell growth procedure included the carbon source and the culture incubation period before cell harvest, while variables in the fermentation procedure included cell concentration, glycerol concentration, temperature, and pH.

E. Sample Treatment. To monitor the time courses of each fermentation, 8-ml samples were drawn. A small volume was initially taken from each saample and diluted for biomass analysis. Cells were removed from the remainder by centrifugation before analysis for 3-HPA and glycerol. The portion of centrifugate submitted for the glycerol assay was also filtered through 0.45-μm-pore-size Millex HV units (Millipore Corp.).

F. Biomass Analysis. Cell concentrations were followed by measuring culture turbidity at 620 nm on a Bausch and Lomb Spectronic 2000 spectrophotometer. Samples were diluted as necessary to allow the absorbance reading to fall between 0.050 and 0.500, a range where absorbance is directly proportional to biomass concentration. Dry cell mass concentration (b) could be determined from absorbance (A) and the relationship b=kA where the constant k was equal to g/l as determined from the slope of a standard curve of b versus A. Data for the standard curve were obtained by measuring optical densities and weights of cells from aliquots drawn from batch cultures at various points in time along the course of growth.

G. 3-HPA Analysis. The assay for 3-HPA content was based on the colorimetric method of Circle et al., *Industrial Engineering Chemical Analysis Ed.* 17: 259–262 (1945), a method that is specific for acrolein detection. 3-HPA is first dehydrated to acrolein which in turn reacts with tryptophan to form a purple complex that absorbs light at 560 nm. Since 3-HPA is not commercially available, acrolein purchased from Eastman Kodak Co. (Rochester, N.Y.) was used to standardize the assays. Assuming 1 mole of 3-HPA dehydrates to 1 mole of acrolein, the absorbance data were expressed in terms of 3-HPA concentration.

Tryptophan reagent consisting of 2.05 g of D, L-tryptophan, 4.17 ml of concentrated HCl, and 2.5 ml of toluene per liter was prepared. In test tubes, 3 ml of properly diluted centrifugate (or acrolein standard) was combined with 6 ml of concentrated HCl and 1.5 ml of tryptophan reagent. Duplicate tubes were incubated at 40° C for 20 minutes as the purple color developed and became stable. Absorbance was measured immediately at 560 nm on a Bausch and Lomb Spectronic 2000 spectrophotometer. The color was stable for approximately 15 minutes and could be maintained for at least 1 hour by cooling the tubes in an ice bath.

H. Glycerol Analysis. To prepare for gas chromatography analysis, one ml of cell-free sample was dried in an oven at 105° C for 24 h. To this residue 1 ml of pyridine and 1 ml of acetic anhydride was added. The resulting reaction mixture was placed in a steam cabinet at 100° C. for 1 hour to allow complete conversion of glycerol to its triacetate derivative. After cooling the sample to room temperature, separation and quantitation of the triacetate derivative was performed with a Varian gas chromatograph, helium carrier gas at 80 psi, injection temperature at 180° C., column temperature at 150° C., and detector temperature at 200° C. The retention time for glycerol triacetate was 3.0–3.2 minutes. Solutions of known glycerol content were also derivatized and used to standardize the assay.

I. Fermentation Rate and Yield Calculations. During the first 7 to 10 hours of the semicarbazide-mediated fermentation of glycerol to 3-HPA, the biomass concentration was tYpically constant and the glycerol and 3-HPA concentrations were linear functions of time. Consequently, intitial glycerol consumption rate and initial 3-HPA productivity were calculated from the linear regression slopes of the early glycerol and 3-HPA concentration time courses. Corresponding specific rates were obtained when slopes wee divided by the average biomass concentration over the time interval under consideration. Initial instantaneous yield was taken to be the ratio of the initial 3-HPA production and glycerol consumption rates. This ratio corresponded to the mass of 3-HPA produced per mass of glycerol consumed in the first few hours of fermentation. Over the course of 3-HPA production, the 3-HPA concentration usually progressed to a peak value and then declined with time. The overall 3-HPA yield was obtained from the peak 3-HPA concentration divided by the glycerol concentration consumed by that point in time. If all of the glycerol were converted to 3-HPA, a maximum yield of 0.8 g of 3-HPA per g of glycerol would occur. Therefore, the percentage of glycerol converted to 3-HPA was obtained by dividing the maximum 3-HPA yield by 0.80 and then multiplying by 100.

Table 1 shows the production of 3-HPA from glycerol by *K. pneumoniae* NRRL B-4011 as a function of the carbon source supporting cell growth and the ages of cells harvested prior to step 2. As can be seen from the data in Table 1, first step cell growth and dehydratase induction are complete after only 24–48 hours when B-4011 is grown on glycerol. In contrast, when glucose is used as the carbon source, dehydratase formation is repressed. Table 2 shows the production of 3-HPA from glycerol by *K. pneumoniae* NRRL B-4011 as a function of process variables. Each variable was varied independently from the following standard conditions: 30° C., pH 6.2, 26.8 g/liter semicarbazide, 30 g/liter glycerol, and 9.3 g/liter biomass. The optimum conditions were 28° C., 40 g/liter semicarbazide hydrochloride, 70 g/liter glycerol and pH 6.0. Under these conditions, the optimum production rate of 0.83 g/g biomass/hour was obtained with a biomass concentration of 3.10 g/liter. However, peak 3-HPA concentration of 46 g/liter was obtained with a biomass concentration of 14.9 g/liter.

TABLE 1

| Carbon Source (100 g/L) | Age of Cells (h) | Specific 3-HPA Production Rate (g/g/h) | Peak 3-HPA Concentration (g/L) |
|---|---|---|---|
| Glucose | 24 | 0.01 | 0.278 |
|  | 48 | 0.0009 | 0.740 |
|  | 72 | 0.0014 | 0.608 |
| Glycerol | 24 | 0.21 | 13.26 |
|  | 48 | 0.07 | 11.33 |
|  | 72 | 0.11 | 8.41 |
| MRS medium only (no carbon source added) | 24 | 0.035 | 0.813 |

TABLE 2

| Variable Condition | 3-HPA Production Rate (g/g/h) | Peak 3-HPA Concentration (g/L) |
|---|---|---|
| Temperature (°C.) |  |  |
| 25 | 0.21 | 14.36 |
| 28 | 0.28 | 17.37 |
| 30 | 0.39 | 16.25 |
| 32 | 0.15 | 10.77 |
| 37 | 0.11 | 15.10 |
| 40 | 0.05 | 12.20 |
| pH |  |  |
| 3 | 0.0 | 0.013 |
| 4 | 0.01 | 0.19 |
| 5 | 0.29 | 12.55 |
| 6 | 0.50 | 16.62 |
| 7 | 0.43 | 15.28 |
| 8 | 0.24 | 16.79 |
| 9 | 0.33 | 14.50 |
| 10 | 0.39 | 15.78 |
| Semicarbazide |  |  |

TABLE 2-continued

| Variable Condition | 3-HPA Production Rate (g/g/h) | Peak 3-HPA Concentration (g/L) |
|---|---|---|
| hydrochloride (g/L) | | |
| 0 | 0.05 | 1.67 |
| 10 | 0.21 | 7.09 |
| 20 | 0.39 | 12.70 |
| 30 | 0.53 | 17.90 |
| 40 | 0.65 | 20.40 |
| 50 | 0.60 | 18.00 |
| Glycerol (g/L) | | |
| 30 | 0.35 | 17.2 |
| 50 | 0.41 | 16.6 |
| 70 | 0.51 | 16.2 |
| 90 | 0.32 | 15.2 |
| 110 | 0.39 | 17.0 |
| 130 | 0.32 | 14.78 |
| 150 | 0.19 | 12.28 |
| Cell Biomass (g/L) | | |
| 1.55 | 0.34 | 2.63 |
| 3.10 | 0.49 | 10.00 |
| 4.65 | 0.20 | 8.73 |
| 6.20 | 0.17 | 7.35 |
| 7.75 | 0.13 | 9.42 |
| 9.30 | 0.12 | 10.27 |
| 12.4 | 0.09 | 10.25 |
| 15.5 | 0.07 | 9.65 |

It is understood that the foregoing detailed description is given merely by way of illustration and that modification and variations may be made therein without departing from the spirit and scope of the invention.

We claim:

1. A method for the production of 3-hydroxypropionaldehyde (3-HPA) from glycerol, which comprises culturing the bacterium *Klebsiella pneumoniae* NRRL B-4011 or subcultures thereof, under aerobic conditions, in an aqueous nutrient medium containing an amount of glycerol effective for the induction of glycerol dehydratase and the production of a recoverable quantity of 3-HPA, and an amount of semicarbazide hydrochloride sufficient to prevent the conversion of 3-HPA to trimethylene glycol, until a recoverable quantity of 3-HPA is produced.

2. The method of claim 1 wherein said bacterium is first grown in an aqueous nutrient medium contaning a carbon source which induces the production of dehydratase enzyme and further incubated in an aqueous medium containing glycerrol and semicarbazide hydrochloride.

3. The method of claim 2 wherein said carbon source is glycerol, 1,2-propanediol, or 1,2-ethanediol.

* * * * *